US009415189B2

(12) United States Patent
Nikou et al.

(10) Patent No.: US 9,415,189 B2
(45) Date of Patent: Aug. 16, 2016

(54) METHOD AND APPARATUS FOR INTRAOPERATIVE CARDIAC TISSUE INJECTION

(75) Inventors: Constantinos Nikou, Monroeville, PA (US); Adam Hahn, Pittsburgh, PA (US); Adam Simone, Pittsburgh, PA (US)

(73) Assignee: Blue Belt Technologies Inc., Pittsburgh, PA (US)

( * ) Notice: Subject to any disclaimer, the term of this patent is extended or adjusted under 35 U.S.C. 154(b) by 1033 days.

(21) Appl. No.: 13/182,406

(22) Filed: Jul. 13, 2011

(65) Prior Publication Data
US 2012/0016339 A1 Jan. 19, 2012

Related U.S. Application Data

(60) Provisional application No. 61/363,998, filed on Jul. 13, 2010.

(51) Int. Cl.
*A61M 25/01* (2006.01)
*A61M 25/00* (2006.01)
(Continued)

(52) U.S. Cl.
CPC ....... *A61M 25/0136* (2013.01); *A61M 25/0069* (2013.01); *A61B 5/0422* (2013.01); *A61B 5/062* (2013.01); *A61B 2017/00022* (2013.01); *A61B 2017/306* (2013.01); *A61B 2034/2051* (2016.02); *A61M 25/0127* (2013.01); *A61M 25/0147* (2013.01); *A61M 2025/004* (2013.01);
(Continued)

(58) Field of Classification Search
CPC ..................... A61M 25/0136; A61M 25/0147; A61M 2025/0092; A61M 2025/0036; A61M 2025/004; A61M 25/0127; A61M 25/0069; A61M 25/014; A61B 19/5244; A61B 2017/306; A61B 5/062; A61B 2017/00022; A61B 5/0422; A61B 2019/5251; A61B 2034/2051
USPC ........................................ 600/424; 604/95.01
See application file for complete search history.

(56) References Cited

U.S. PATENT DOCUMENTS 4,578,061 A 3/1986 Lemelson
5,797,849 A 8/1998 Vesely et al.
(Continued)

FOREIGN PATENT DOCUMENTS

EP 1 205 156 A2 5/2002
WO WO-2005016157 A1 2/2005
(Continued)

OTHER PUBLICATIONS

Machis, Michael P., Igo, Stephen H., Min Inv. Access of the Normal Pericardium: Initial Clin. Exp. with a Novel Device, Clin.Cardiol., 1999, I-36-I-39, vol. 22 (Suppl. I).
(Continued)

*Primary Examiner* — Bhisma Mehta
*Assistant Examiner* — Brandy S Lee (57) ABSTRACT

The apparatus provides for injecting therapeutic agents at precise locations into the bodily tissue. The apparatus comprises an end effector that is guided to a precise location by motion controllers on a handle. At a precise location, the end effector attaches via a vacuum to the cardiac tissue. A flexible needle is advanced through a deflecting tunnel in the end effector to a desired depth. A therapeutic agent is then introduced via the flexible needle into the cardiac tissue. All these manipulations can be controlled by one hand and can be viewed via imaging methods.

23 Claims, 7 Drawing Sheets

(51) Int. Cl.
  *A61B 5/042* (2006.01)
  *A61B 5/06* (2006.01)
  *A61B 17/00* (2006.01)
  *A61B 17/30* (2006.01)

(52) U.S. Cl.
  CPC .............. *A61M2025/0036* (2013.01); *A61M 2025/0092* (2013.01)

(56) References Cited

U.S. PATENT DOCUMENTS

| | | |
|---|---|---|
| 5,827,216 A | 10/1998 | Igo et al. |
| 5,972,013 A | 10/1999 | Schmidt |
| 6,309,370 B1 | 10/2001 | Haim et al. |
| 6,319,230 B1 | 11/2001 | Palasis et al. |
| 6,589,166 B2 | 7/2003 | Knight et al. |
| 6,591,129 B1 | 7/2003 | Beh-Haim et al. |
| 6,592,552 B1 | 7/2003 | Schmidt |
| 6,606,513 B2 | 8/2003 | Lardo et al. |
| 6,659,950 B2 | 12/2003 | Taheri |
| 6,666,844 B1 | 12/2003 | Igo et al. |
| 6,685,648 B2 | 2/2004 | Flaherty et al. |
| 6,709,427 B1 | 3/2004 | Nash et al. |
| 6,716,196 B2 | 4/2004 | Lesh et al. |
| 6,796,963 B2 | 9/2004 | Carpenter et al. |
| 6,834,201 B2 | 12/2004 | Gillies et al. |
| 6,890,295 B2 | 5/2005 | Michels et al. |
| 6,969,371 B2 | 11/2005 | Palasis et al. |
| 7,083,630 B2 * | 8/2006 | DeVries ........... A61B 17/06109 128/898 |
| 7,106,574 B2 | 9/2006 | Beyerlein |
| 7,146,225 B2 | 12/2006 | Guenst et al. |
| 7,335,158 B2 | 2/2008 | Taylor |
| 7,338,434 B1 | 3/2008 | Haarstad et al. |
| 2003/0028172 A1 | 2/2003 | Epstein et al. |
| 2005/0154376 A1 | 7/2005 | Riviere et al. |
| 2005/0261662 A1 * | 11/2005 | Palasis et al. ................. 604/506 |
| 2008/0009747 A1 * | 1/2008 | Saadat et al. .................. 600/471 |
| 2008/0294096 A1 * | 11/2008 | Uber et al. ...................... 604/66 |
| 2010/0256523 A1 * | 10/2010 | Uznanski ......... A61B 17/00234 600/565 |

FOREIGN PATENT DOCUMENTS

| | | |
|---|---|---|
| WO | WO-2007062632 A1 | 6/2007 |
| WO | 2007/103258 A2 | 9/2007 |
| WO | WO-2008071367 A1 | 6/2008 |
| WO | 2010/002604 A1 | 1/2010 |

OTHER PUBLICATIONS

Supplementary Partial European Search Report dated Feb. 26, 2014.

* cited by examiner

METHOD AND APPARATUS FOR INTRAOPERATIVE CARDIAC TISSUE INJECTION

CROSS-REFERENCE TO RELATED APPLICATIONS

This application claims priority to U.S. Provisional Application Ser. No. 61/363,998, filed on Jul. 13, 2010 and entitled "Method and Apparatus for Intraoperative Cardiac Tissue Injection." Priority to this prior application is expressly claimed and the disclosure of that application is hereby incorporated herein by reference in its entirety.

FIELD OF THE INVENTION

This invention relates generally to the field of minimally invasive surgery and, more particularly, to the delivery of a drug or tissue-engineered material to the heart via direct injection.

BACKGROUND OF THE INVENTION

As medical and technical knowledge advances, there are a growing number of situations where there may be significant therapeutic value in having the ability to inject a drug or tissue-engineered material directly into a precise location on the epicardium of a patient. An example of one such situation is the infusion of therapeutic agents, such as radioactive compounds, for the treatment of tumors. With respect to tissue-engineered materials, stem cells and biopolymers have been injected into the heart in order to treat, for example, myocardial infarct lesions. Until relatively recently, however, the delivery of these substances had necessitated the cracking open of the rib cage of a patient to access the heart directly due to the fact that the heart is extremely well-protected and difficult to access. For a variety of reasons, including the possibility for infection and long recovery times, a minimally invasive procedure where the heart is accessed from below the xiphoid process is preferred.

While the access problem has been solved for certain procedures, the performance of surgical procedures on the heart remains a technical challenge not only because the surgeon cannot directly see the heart during the operation, but also because the heart continues to move during the procedure. The movement caused by pumping makes it extraordinarily difficult to achieve any accuracy in the location of the injection when using prior art minimally invasive prior art devices.

One prior art device, the PerDUCER pericardial access device, is presently used for minimally invasive access to the pericardial space, whether to insert a guide wire, inject a drug or withdraw some pericardial fluid when indicated. As disclosed in the art, the device comprises a 21-gauge needle housed inside a 12-French stainless steel sheath tube that is about 20 cm in length. The distal end of the sheath tube is bonded to a plastic tube with a tapered end and a half-moon cross-sectional shape. The tapered end of the plastic tube further has a hemispherical side hole that is pressed against the pericardium during the procedure. A vacuum suction is then applied to the side hole, which forces a portion of the pericardium to be pulled into the side hole and creates a bleb. A guide wire or other sharp device is then introduced into the bleb to permit direct injection directly into the pericardial space or to allow for future access. A drawback to this device, however, is that it does not permit injection or entry into the pericardium at an exact, predetermined location and depth due to the distortion of the pericardium caused by the formation of the bleb. Moreover, this device does not permit injection into the epicardium.

In view of the foregoing, a need has been recognized in connection with improving upon the shortcomings and disadvantages of current systems and methods for delivering injections or other therapeutic agents to a precise location within the pericardial sac or into the epicardium itself.

For a better understanding of the present invention, together with other and further features and advantages thereof, reference is made to the following description, taken in conjunction with the accompanying drawings, and the scope of the invention that will be pointed out in the appended claims.

DESCRIPTION OF THE PREFERRED EMBODIMENTS

The present invention provides an improved system and apparatus for intraoperative cardiac injection. FIG. 1 shows the components of a system 10 for delivering injections or other therapeutic agents to a precise location within the pericardial sac or into the epicardium itself. Specifically, the system includes a control handle 20 having a proximal end 30 and a distal end 40. The distal end 40 is attached to a flexible catheter 50 having a proximal end 60 and a distal end 70. While the proximal end of the catheter 50 is attached to the handle 20, preferably via an introducer (not shown) as is known in the art, an end effector 80 of the present invention is disposed on the distal end 70.

The Handle

Figures 1A, 1B:
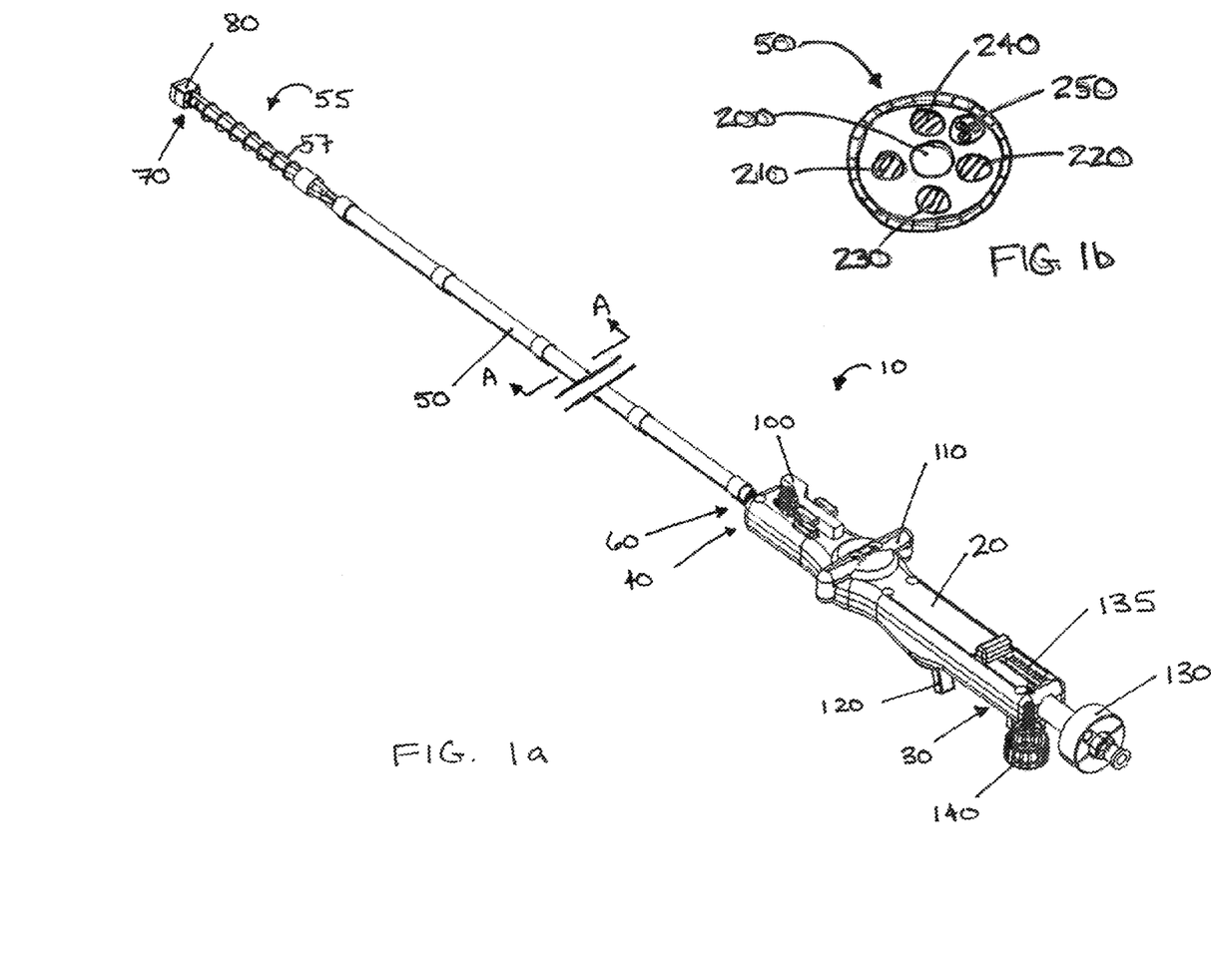
FIG. 1a is a perspective view of a system for intraoperative injection into cardiac tissue according to features of the invention.
FIG. 1b is a cross-sectional view, taken along the lines A-A of FIG. 1a, of the elongated catheter of the present invention.

In a preferred embodiment all manipulations can be controlled the surgeon using only one hand. Handle 20 comprises a vacuum port switch 100 that is attached to a vacuum tube 200 as is illustrated in FIG. 1 a and permits the surgeon to selectively apply suction to affix the end effector 80 to heart tissue when it is in the desired position adjacent the heart. In an alternative embodiment, the surgeon could activate the vacuum by a foot pedal mechanism that acts upon the vacuum port switch.

Figure 2A:
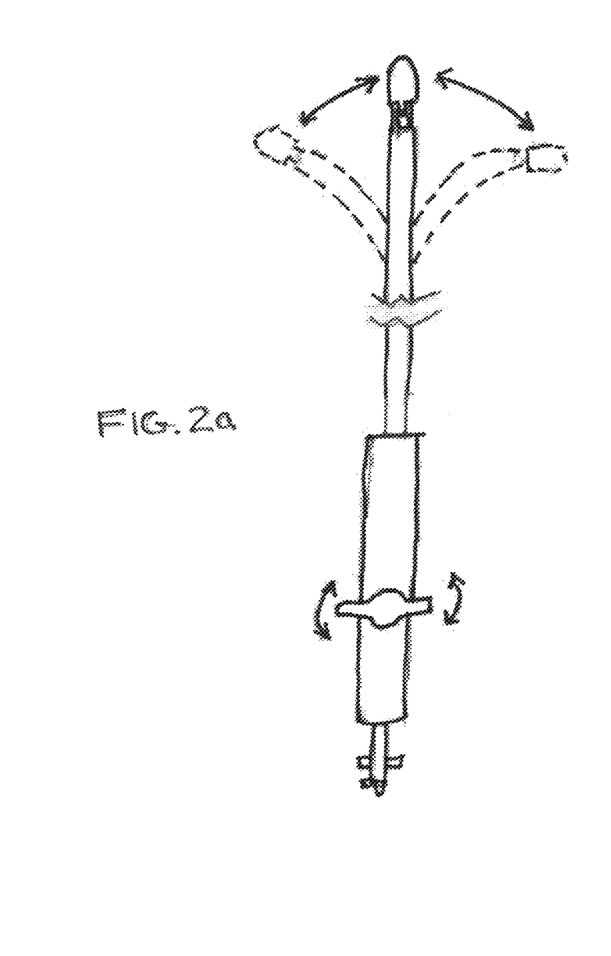
FIG. 2a is a plan view of the system of the present invention demonstrating lateral steerability of the elongated catheter.
Figure 2B:
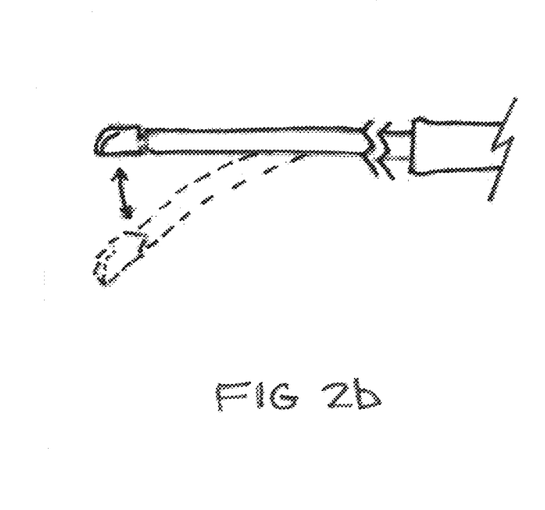
FIG. 2b is a side elevational view of the system of the present invention demonstrating vertical steerability of the elongated catheter.

Referring, now, to FIGS. 1, 1a, 2a, 2b, and 3, the handle 20 also has a planar motion controller 110 that is rigidly connected to a left guide wire 210 and a right guide wire 220, both of which are disposed upon the end effector 80 such that when the planar motion controller 110 is twisted in a counter-clockwise direction, the left guide wire 210 will pull on the end effector 80 at the left guide wire attachment point 410 and steer it laterally to the left. Likewise, twisting the planar motion controller 110 in a clockwise direction will cause the right guide wire 220 to pull on the end effector 80 at the right guide wire attachment point 420 and steer it laterally to the right. FIG. 2a demonstrates this lateral movement.

The handle 20 also comprises a vertical motion trigger 120 that is connected to a lower guide wire 230. The lower guide wire 230 is also connected to the lower guide wire attachment point 430 such that when the surgeon pulls the trigger 120, the lower guide wire 230 causes the end effector 80 to deflect vertically downward in a direction generally orthogonal to the deflection induced by the left guide wire 210 or the right guide wire 220. This vertical movement is demonstrated by FIG. 2b. In the preferred embodiment, frictional elements are used to maintain the end effector in the deflected vertical or lateral positions. Surgeons can then manually return the end effector to its original position when they desired. In an alternative embodiment, the planar motion controller 110 and the vertical motion trigger 120 are spring-loaded so that when the controller 110 or trigger 120 is not being activated, end effector 80 will automatically return to a neutral, non-deflected position.

The proximal end 30 of the handle 20 comprises a needle injector controller 130 that is connected to a flexible needle 240 such that axial advancement of the controller 130 results in axial advancement of the needle 240. Automatic extension mechanisms known in the art such as motorized computer controlled mechanism may also be employed to axially advance the needle a predetermined distance. Alternatively, the controller 130 can be constructed so that axial advancement of the needle 240 is manually accomplished via clockwise rotation of the controller 130 in screw-like fashion, via a foot pedal mechanism (not shown) or via a ratchet mechanism (not shown) as is well-known in the art. Where a ratchet mechanism is used, it is preferred that each advancement increment be in the range of 0.25 mm and 0.75 mm. Regardless of the method for advancement of the needle 240, the needle injector controller 130 also comprises an advancement measuring indicator 135 that enables the surgeon to know how far the needle 240 has been advanced during surgery. There are many such advancement measuring indicators that are well known in the art. The status of this advancement measuring indicator may be either manually or automatically determined and can be input into a computer navigation system that, in a preferred embodiment, would graphically display the needle advancement status along side of, or overlaid onto, the user interface screen of the computer navigation system. The display, for example, could be either a simple numerical readout or a photorealistic computer rendering of the device with the needle extended the measured distance out of the end effector, and preferably, into the heart or other tissue.

In some embodiments, a needle lock mechanism 140 is included on the handle 20 for fixing the needle 240 in place once it has been inserted into the desired location in the heart. Once the needle 240 is in the desired location, a therapeutic agent can be injected via an injection port (not shown). In embodiments using a ratcheting mechanism, the mechanism keeps the needle in place until the user desires to remove it, at which point, a spring-loaded release mechanism retracts the needle.

The Catheter

In a preferred embodiment, the catheter 50 of the present invention carries a vacuum tube 200, a flexible injection needle 240, guide wires 210, 220, 230 to facilitate intended movement, in two dimensions, of the end effector 80, and sensor wires 250. A distal portion of the catheter 50 includes a steerable portion 55 comprised of a series of disks 57 that ensure smooth bending while the end effector 80 is being steered and also keeps the guide wires close to the needle 240 providing for a balanced distribution enabling a balanced movement.

The End Effector

Figure 3:
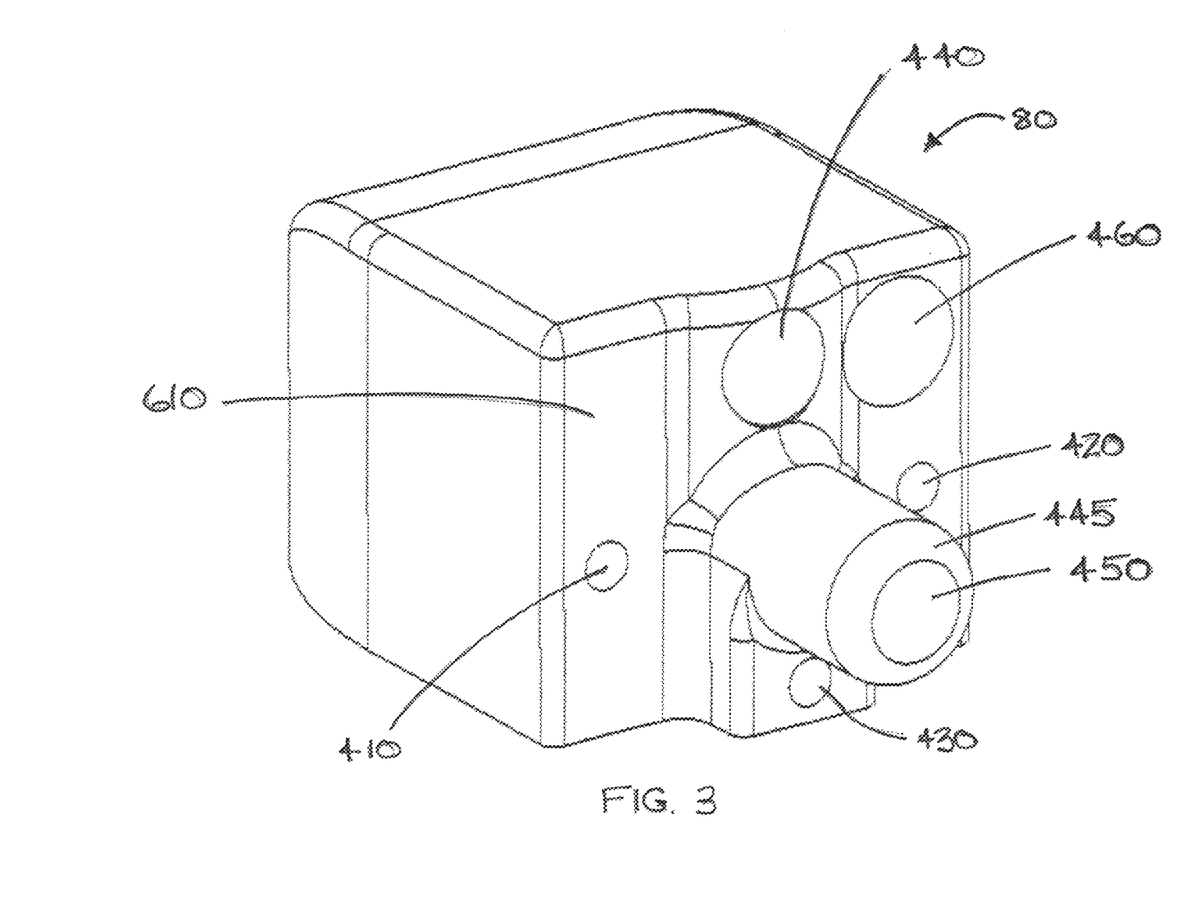
FIG. 3 is an enlarged top isometric view of the end effector of the system of the present invention.
Figure 4A:
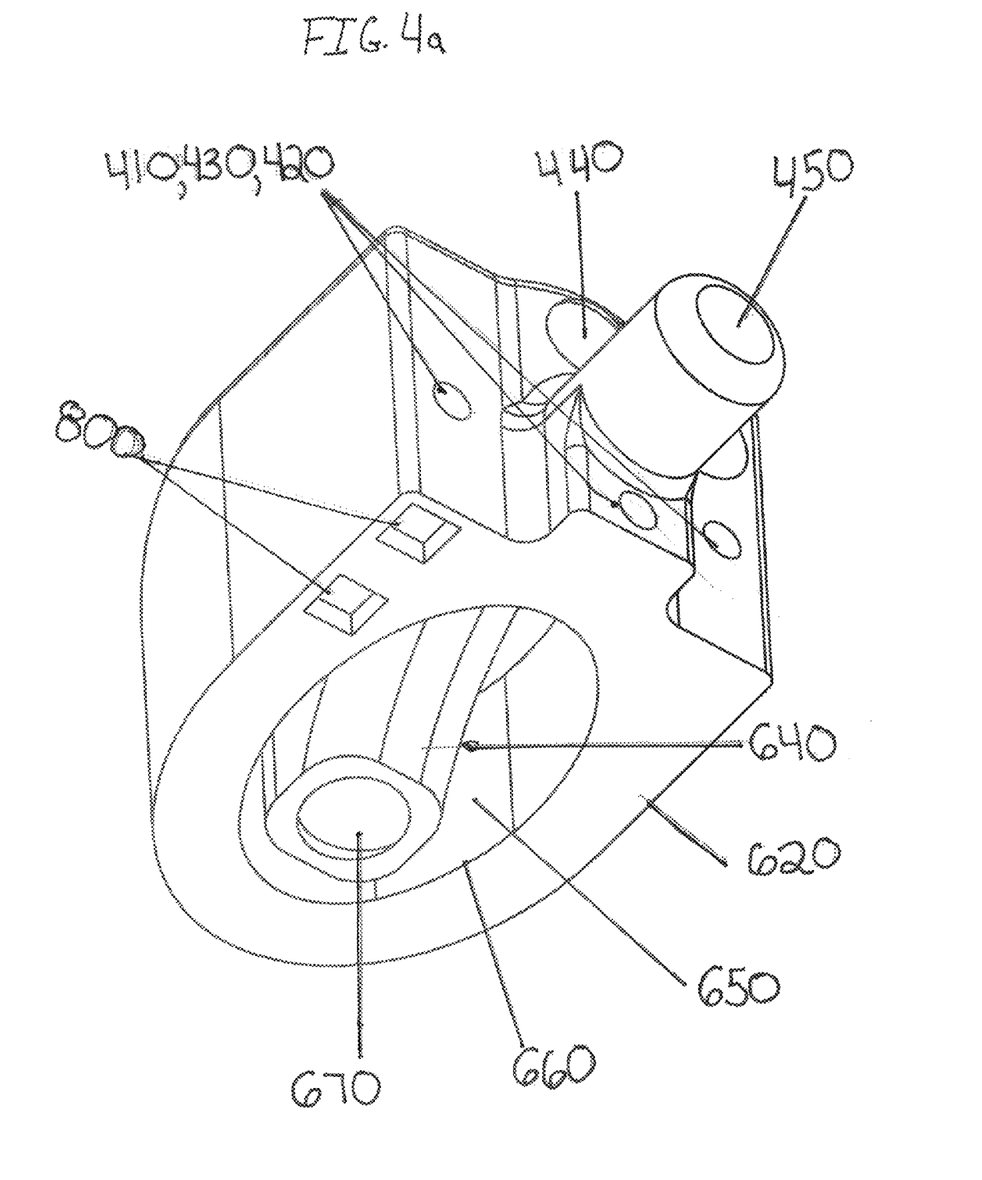
FIG. 4a is an enlarged bottom isometric view of a first preferred embodiment of the end effector of the system of the present invention.
Figure 4B:
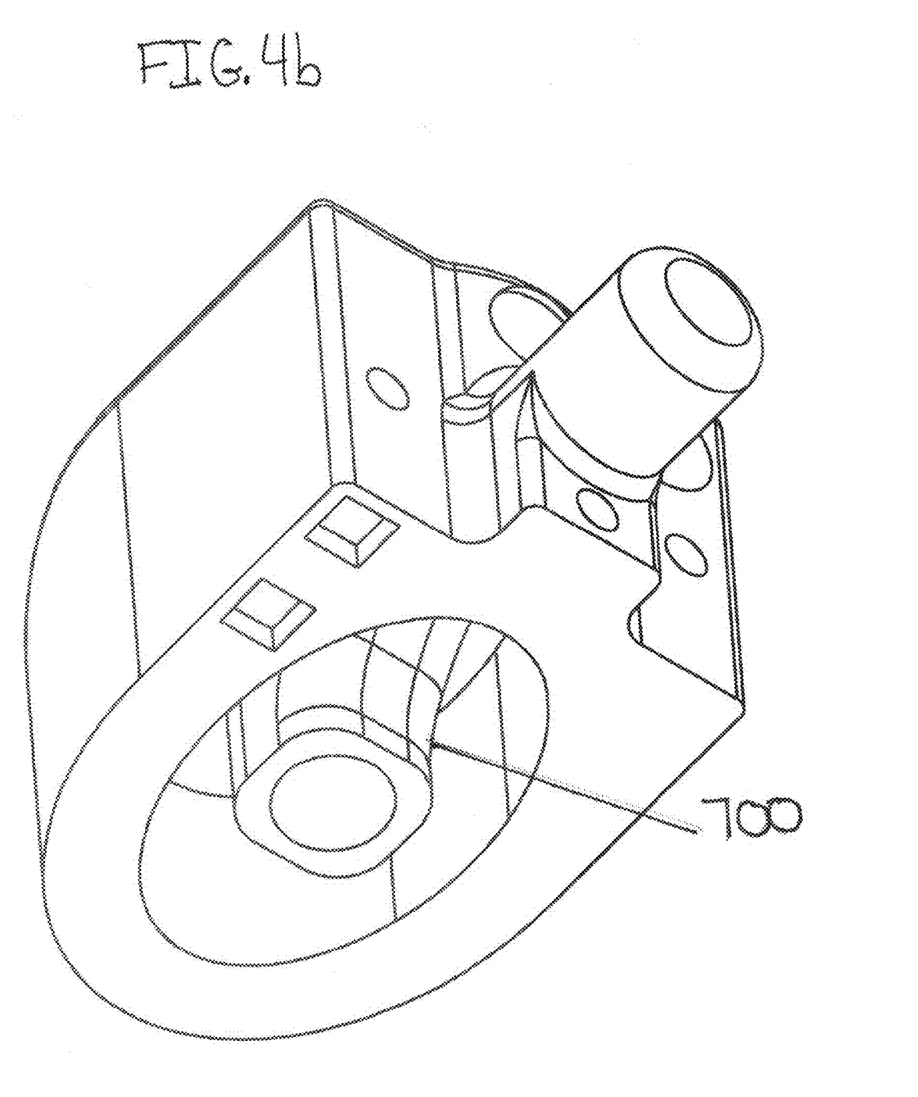
FIG. 4b is an enlarged bottom isometric view of second preferred embodiment of the end effector of the system of the present invention.
Figure 5:
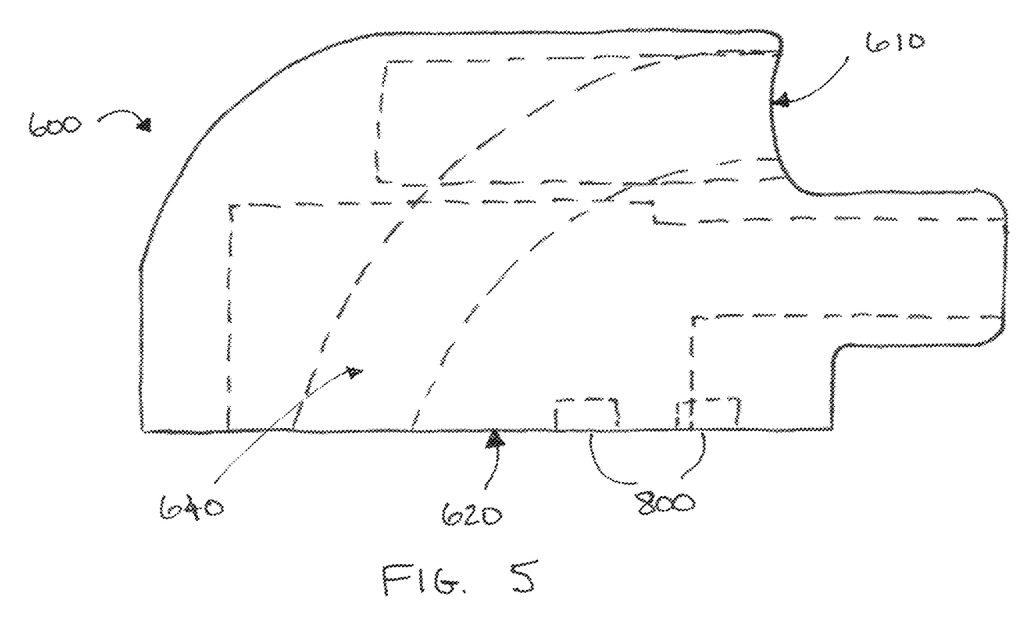
FIG. 5 is an enlarged side elevational view of the end effector shown in FIG. 4a of the system of the present invention.

Referring now to FIGS. 3-5, the end effector 80 of the present invention has a leading face 600, a trailing face 610, and a working face 620. The end effector can be made out of any bio-compatible plastic that is substantially rigid or metal material known in the art. For example, a dense silicone which is a stiff, yet still pliable material is advantageous for vacuum adhesion. While the end effector 80, as a whole, is generally rectangular in a plane parallel to the trailing face 610, the leading face 600 is largely rounded to facilitate insertion into the body of a patient. Other shapes that are possible will be apparent to those skilled in the art.

In addition to the guide wire attachment points 410, 430, 420 previously discussed, the trailing face 610 also comprises an injection needle port 440, a vacuum port 450 and a sensor cavity 460.

The sensor cavity 460 houses an electromagnetic sensor coil (not shown) for electromagnetic tracking of the precise 6 degree-of-freedom (6DOF) position of the end effector 80 during a procedure. Knowledge of the sensor position relative to the patient's body, in conjunction with its position within the end effector 80, can provide very precise real-time information in relation to navigation and positioning of the end effector 80 for injection.

In a preferred embodiment, the vacuum port 450 is housed in a protrusion 445 that slidingly couples with the vacuum tube 200 to selectively provide suction to the heart surface and immobilize the end effector 80 relative to the heart. The vacuum port 450 provides access to an interior vacuum chamber 650 that creates a suction aperture 660 on the working surface 620. The cross-sectional area of the suction aperture 660 is large in comparison to the cross sectional area of the working surface 620 overall. This comparatively large aperture 660 enables secure fixation of the end effector 80 upon the heart when desired. Other methods of providing suction to the tissue surface are well-known to those skilled in the art.

In FIG. 4a, the injection needle port 440 receives the needle 240 into a deflecting tunnel 640 that comprises an arced tunnel between the trailing face and the working face 620. In this preferred embodiment, the tunnel 640 will deflect the needle 240 passing through it at an approximately forty-five degree angle. It is the deflection of the needle 240 from a plane substantially parallel to the surface of the patient's heart to a plane orthogonal or nearly orthogonal to the surface of the heart that obviates the need for the creation of a bleb as in prior art systems and allows better accuracy in injection location into the epicardium or pericardium. The deflection tunnel 640 emerges from within the vacuum chamber 650 toward the suction aperture 660 on working surface 620. This allows the vacuum to surround the working surface port 670 creating a tight seal and preventing the working face 620 from peeling up and breaking the suction when the needle is extended. The needle 240 emerges from the deflecting tunnel 640 at the working surface port 670, which, when in use, is pressed against the pericardium. In this way, the needle 240 enters cardiac tissue. In FIG. 5, an enlarged side elevational view of the end effector embodiment illustrated in FIG. 4*a* is shown from a different angle. Those skilled in the art will readily recognize that the deflecting tunnel can be changed in a suitable range, which will result in a slightly modified drawing from this angle.

In an alternative preferred embodiment, the deflection tunnel 700 deflects the needle an approximately ninety degree angle as seen in FIG. 4*b*. It can be seen that many different deflection angles are possible, and within the scope of the present invention. A limiting factor, however, may be the limits of how far the needle can be bent, and still function properly, within the apparatus of the invention.

In another embodiment, the end effector 80 also comprises a pair of sensors 800, which provide important information about the near-field properties of interest of the cardiac tissue with which they come into contact. For example, necrotic tissue will have a different conductance than healthy tissue. One example of an electro-anatomic mapping sensor system that could be used is the CARTO system by Biosense, though any suitable sensor system known in the art can also be used. It is also possible, with these or other sensors deployed on the end effector, to gain information about any electrical, electromagnetic, chemical or biological properties that might be desired by the health care provider. It is a simple matter to run the wires for these sensors through the catheter 50 as demonstrated for other sensor wires in FIG. 1*b*.

Use of the System of the Invention

Figure 6:
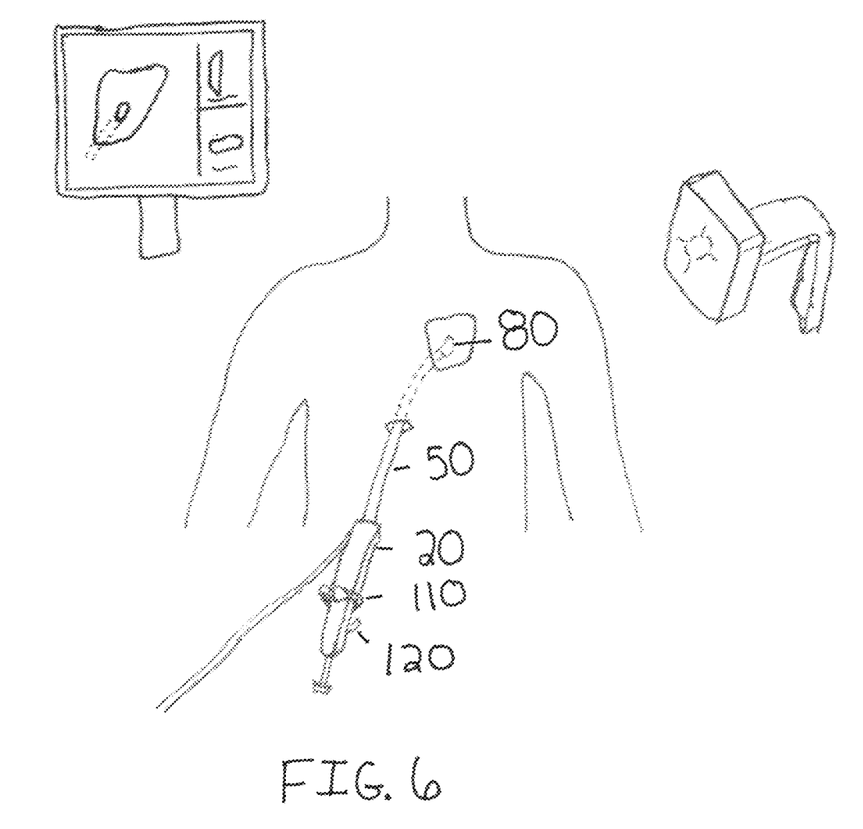
FIG. 6 is a diagrammatic illustration of the system of the present invention as it is used in surgery.

As illustrated in FIG. 6, the end effector 80 and catheter 50 are inserted into a patient via the well-known sub-xiphoid access point. The end effector 80 is then guided by the surgeon to the general area of the pericardium. In order to maneuver the end effector 80 into a desired location, the surgeon watches the imaged heart on a monitor that is obtained via fluoroscopy or some other imaging method and compares it to the real-time data supplied by the electromagnetic sensor coil in the end effector 80, which is mapped onto the imaged heart so the surgeon knows where and in what orientation the end effector 80 is at all times in relation to the beating heart. Furthermore, the location and extension of the needle, as determined by the advancement measurement indicator described above, may be mapped onto the heart images as well. The coordinate mapping between the coordinates of the electromagnetic tracking system and coordinate frame of any preoperative or intra-operative heart images may be established with so-called "registration" techniques which are well demonstrated by numerous inventions and publications, and are readily apparent to those skilled in computer-assisted surgery techniques.

While the surgeon uses the planar motion controller 110 and the vertical motion trigger 120 on the handle 20 to maneuver the end effector 80 into a predetermined location, the sensors 800 provide valuable information about the pericardial tissue with which the surgeon can make additional last-minute decisions.

Once the surgeon is satisfied that the end effector 80 is in the desired position, the vacuum can be activated either via the port switch 100 on the handle 20 or, alternatively, via a foot pedal mechanism, which causes suction to be applied to the pericardium at the working surface port 670, thus temporarily fixably attaching the end effector 80 to the cardiac tissue and enabling the surgeon to have complete confidence in the precise location of the injection. Next the surgeon will advance the needle. This can be done via an automated computer system, a foot pedal system, or manually using a preferred embodiment such as the needle injector controller 130 to advance the needle 240 through the tunnel 640 and into the tissue, lock it into place using the needle lock mechanism 140, and inject the desired therapeutic agent.

If not otherwise stated herein, it is to be assumed that all patents, patent applications, patent publications and other publications (including web-based publications) mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. Accordingly, the drawings and description are to be regarded as illustrative in nature, and not as restrictive.

What is claimed is:

1. An improved apparatus for injecting a therapeutic agent into cardiac tissue at a precise location wherein the apparatus comprises a handle, a catheter, an end effector and a flexible needle;

the handle comprising a set of motion controllers, including a means for advancing the flexible needle;

the catheter comprising a means for carrying a vacuum tube, the flexible needle, and a set of guide wires; wherein the motion controllers manipulate the set of guide wires to guide the end effector to the precise location; the catheter further having a longitudinal axis;

the end effector having a proximal end and a distal end comprising at least a leading face at its distal end, a trailing face at its proximal end, where it is connected to the catheter, and a working face disposed in a sidewall between, and substantially orthogonal to, the leading face and the trailing face; a suction aperture formed in the working face is in fluid communication with a vacuum port in the trailing face; the vacuum port fittingly coupled with the vacuum tube carried in the catheter, for selectively affixing the end effector to the cardiac tissue using suction, wherein the direction of suction flow is substantially orthogonal to the longitudinal axis of the catheter;

a deflecting needle tunnel extending from an injection needle port on the trailing face to a working face needle port;

whereby advancement of the flexible needle through the tunnel causes the needle to be deflected at an angle before emerging from the needle tunnel at the working face needle port and penetrating the cardiac tissue when extended.

2. The improved apparatus of claim 1 wherein advancement of the flexible needle through the tunnel causes the needle to be deflected at an angle in the range of 45 to 90 degrees.

3. The improved apparatus of claim 1, wherein the end effector further comprises a positional tracking device to enable real-time tracking and navigation.

4. The improved apparatus of claim 3, wherein in the positional tracking device is an electromagnetic sensor coil.

5. The apparatus of claim 1 further comprising a means for locking the flexible needle into position.

6. The improved apparatus of claim 1, wherein the end effector further comprises a plurality of sensors for providing information about the tissue.

7. The improved apparatus of claim 1 wherein the end effector may be intentionally directed in at least one dimension.

8. The improved apparatus of claim 1, further comprising an advancement measurement indicator for determining how far the flexible needle has been advanced.

9. The improved apparatus of claim 8, wherein data from the advancement measurement indicator can be correlated with computer navigation system data to provide real time positional information about the needle.

10. The improved apparatus of claim 1, wherein advancement of the needle and manipulation of the guide wires can be performed by the surgeon with one hand via manipulation of the means on the handle.

11. The improved apparatus of claim 1, wherein the catheter further comprises a distal steerable portion comprised of a series of disks to enable smooth bending while steering the end effector.

12. The improved apparatus of claim 1, wherein the cross-sectional area of the suction aperture is of a sufficient size, and the working face needle port within the section aperture is a sufficient distance from the outer edge of the suction aperture, such that the end effector does not form a bleb in the tissue adjacent to the working needle face port.

13. The handle of claim 1, further comprising means for injecting the therapeutic agent into the tissue.

14. A method of injecting a therapeutic agent into cardiac tissues at a precise location, the method comprising:
    (a) selecting an injecting instrument comprising:
    a handle, a catheter, an end effector and a flexible needle;
    the handle comprising a set of motion controllers, a means for advancing the flexible needle;
    the catheter comprising a means for carrying a vacuum tube, the flexible needle, a set of guide wires, and a longitudinal axis;
    the motion controllers manipulate the set of guide wires to guide the end effector to the precise location;
    the end effector having a proximal end and a distal end comprising;
    at least a vacuum chamber, a leading face at the distal end, a trailing face at the proximal end, and a working face in a sidewall between, and substantially orthogonal to, the distal and proximal ends; the vacuum chamber having a first end terminating in a suction aperture formed in the working face for selectively affixing the end effector to the tissue and a second end terminating in a vacuum port in the trailing face; the vacuum port fittingly coupled with the vacuum tube in the catheter;
    a deflecting arcuate needle tunnel extending from an injection needle port on the trailing face to a working face needle port on the working face,
    whereby advancement of the flexible needle through the tunnel causes the needle to be deflected at an angle before exiting the tunnel;
    (b) positioning the end effector with the motion controllers at the precise location on the cardiac tissue;
    (c) applying a vacuum force through the vacuum port to the suction aperture to affix the end effector at the precise location on the cardiac tissues, such that the direction of the vacuum force on the cardiac tissue is substantially orthogonal to the longitudinal axis of the catheter;
    (d) advancing the flexible needle with the motion controllers a measured distance through the working face port into the tissue to a desired depth, and introducing a therapeutic agent via the flexible needle into the tissue.

15. The method of claim 14, wherein advancement of the flexible needle through the tunnel causes the needle to be deflected at an angle in the range of 45 to 90 degrees.

16. The method of claim 14, wherein the end effector further comprises a positional tracking device to enable real-time tracking and navigation.

17. The method of claim 14 wherein the end effector further comprises a pair of sensors on the working face for providing information about properties of interest.

18. The method of claim 14, wherein the end effector may be intentionally directed in at least one direction.

19. The method of claim 14, further comprising using an advancement measurement indicator to determine the distance the flexible needle has been advanced.

20. The method of claim 19, further comprising using data from the advancement measurement indicator to correlate with computer navigation system data providing real time positional information about the needle in relation to the cardiac tissue.

21. The method of claim 14, wherein the catheter further comprises a distal steerable portion comprised of a series of disks to enable smooth bending while steering the end effector.

22. The method of claim 14, wherein the handle further comprises a means for locking the flexible needle into position.

23. The method of claim 14, wherein the handle further comprises a means for injecting the therapeutic agent into the cardiac tissue.

* * * * *